United States Patent [19]

Barth et al.

[11] 4,295,301
[45] Oct. 20, 1981

[54] DRESSING APPARATUS WITH MEANS FOR DETECTING GRINDING WHEEL WEAR

[75] Inventors: Charles F. Barth, Parma; Thomas S. Stelson, Richmond Heights; David E. Blake, Cleveland Heights, all of Ohio

[73] Assignee: TRW Inc., Cleveland, Ohio

[21] Appl. No.: 92,623

[22] Filed: Nov. 8, 1979

[51] Int. Cl.³ ............................................. B24B 53/00
[52] U.S. Cl. ........................... 51/165.88; 125/11 CD
[58] Field of Search ......... 51/165.87, 165.88, 135.5 R; 125/11 R, 11 CD

[56] References Cited

U.S. PATENT DOCUMENTS

| | | | |
|---|---|---|---|
| 2,746,214 | 5/1956 | Alvord | 51/134.5 R |
| 2,986,853 | 6/1961 | Behlen | 51/134.5 R |
| 3,500,811 | 3/1970 | Perkins | 125/11 R |
| 3,560,826 | 2/1971 | Lonaberger | 51/134.5 R |
| 3,590,799 | 7/1971 | Gluchowicz | 125/11 R |
| 3,667,165 | 6/1972 | McDowell | 51/134.5 R |
| 3,691,698 | 9/1972 | Schaller | 51/165.88 |

FOREIGN PATENT DOCUMENTS

633720  11/1978  U.S.S.R. ........................... 51/165.87

*Primary Examiner*—Harold D. Whitehead
*Attorney, Agent, or Firm*—Yount & Tarolli

[57] ABSTRACT

An apparatus senses the extent of actual wear of a grinding wheel at an area where the wear will be the greatest during the grinding of a workpiece. The grinding wheel is dressed by removing material from the grinding wheel to an extent which is a function of the extent of sensed wear at the location where the wear is the greatest. The apparatus includes a probe member which is movable toward the circular working surface or side of the grinding wheel from a retracted position and a detector assembly which detects when the probe member initially engages the circular side of the grinding wheel. In some embodiments of the invention, the probe member is moved toward the grinding wheel in incremental steps with sufficient time between the steps to enable the grinding wheel to rotate through slightly more than one complete revolution. In one embodiment of the invention the detector assembly includes a mass which is connected with a probe member. Upon initial engagement of the probe member with the circular side of the grinding wheel, relative acceleration occurs between the mass and probe member. In another embodiment of the invention the detector assembly includes a load cell which detects the occurrence of deflection upon initial engagement of the probe member with the grinding wheel. In still another embodiment of the invention, the probe member is moved with a wheel dressing tool to detect when a wheel dressing operation has been completed. After a wheel dressing operation has been completed the rotational speed of the grinding wheel is increased to maintain a desired surface speed even though the diameter of the grinding wheel has decreased.

8 Claims, 11 Drawing Figures

DRESSING APPARATUS WITH MEANS FOR DETECTING GRINDING WHEEL WEAR

BACKGROUND OF THE INVENTION

This invention relates generally to apparatus for detecting the extent of wear of a grinding wheel and to apparatus for dressing a grinding wheel.

During operation of a known grinding machine, a grinding wheel is dressed at predetermined intervals during operation of the machine. Although the grinding wheel is rotated at a constant spindle speed during operation of the machine, the surface speed of the grinding wheel is higher when the grinding wheel is new and becomes less as the grinding wheel is worn away due to grinding and wheel dressing operations. When the wheel is new and has a higher surface speed, the rate of wear of the wheel is less than when the diameter of the wheel has been reduced. However, the wheel is dressed to the same extent when the wheel is new as when the wheel becomes worn and has a reduced diameter. In addition, the grinding wheel is commonly overdressed to compensate for the maximum rate of wheel wear which could possibly occur during grinding of a workpiece. This is done without regard for the actual extent of grinding wheel wear. Therefore, excessive material is removed from the grinding wheel during wheel dressing operations.

The removal of excessive material from a grinding wheel during wheel dressing increases the cost of a grinding operation due to the resultant wasting of grinding wheel material and due to the necessity of changing grinding wheels more often during the grinding of a large number of pieces. The changing of the grinding wheels can become particularly onerous when relatively high strength super alloys are being ground. This is because a relatively large volume of the wheel is consumed in order to remove a predetermined volume of material from a workpiece formed of a relatively high strength super alloy.

A probe member has previously been utilized to detect when an abrasive belt becomes worn. Thus, U.S. Pat. No. 3,691,698 discloses a probe or sensing member which is connected with a transducer to determine when an abrasive belt becomes worn. It should be noted that the probe member disclosed in this patent is maintained in continuous engagement with the belt during operation of the belt. This would result in the belt wearing away the probe.

SUMMARY OF THE PRESENT INVENTION

The present invention provides a new and improved method and apparatus which enables a grinding wheel to be accurately dressed without excessive removal of material from the grinding wheel. By accurately dressing the grinding wheel without overcompensating for wear, the volume of abrasive material removed from a grinding wheel during each dressing operation is reduced to thereby reduce the amount of abrasive material which is wasted. By reducing the amount of material which is removed from the grinding wheel during each dressing operation, the rate at which the diameter of the grinding wheel is reduced is decreased with the result that the grinding wheel has a relatively high surface speed for a longer period of time which tends to increase wheel life. Thus, wheel life is increased both by reducing the amount of material which is removed during each wheel dressing operation and due to the fact that the wheel surface speed after each dressing operation is faster than with prior art dressing devices and methods. This enhances the operating life of the grinding wheel and reduces the number of times which a grinding machine must be shut down to change a grinding wheel. The rotational speed of the grinding wheel may advantageously be increased as wheel diameter is decreased to maintain a desired wheel surface speed.

In accordance with a feature of the present invention, the extent of actual wear of a grinding wheel surface in an area where wear is the greatest is sensed. The grinding wheel is dressed by removing material from the grinding wheel to an extent which is a function of the extent of the sensed wear at the location where the wear is the greatest. In order to sense the extent of actual wear of the grinding wheel, a probe member is moved toward the grinding wheel. A detector is provided to detect when the probe member initially engages the circular side surface of the grinding wheel.

In an embodiment of the invention, the detector which detects the initial engagement of the probe member with a grinding wheel is an accelerometer. The accelerometer includes a mass which is connected with the probe member. When the probe member initially engages the grinding wheel, relative acceleration occurs between the mass and probe member. The relative acceleration between the mass and probe member results in an output signal from a piezoelectric material to indicate that the relative acceleration has occurred due to deflection of the probe member by the grinding wheel upon initial engagement of the grinding wheel with the probe member. In another embodiment of the invention, deflection of the probe member due to initial engagement with the grinding wheel is detected by a load cell.

During the use of a grinding wheel, certain areas will wear at a greater rate than others. It is possible by experimentation and/or calculation to determine the areas of a grinding wheel which wear at the greatest rate. In order to fully dress a grinding wheel, the grinding wheel must be dressed to an extent such that the area of greatest wear is dressed to the desired configuration.

In an embodiment of the invention, completion of a wheel dressing operation is detected by detecting when the area of greatest wear is in a predeteriend spatial relationship with a wheel dressing tool. This is accomplished by detecting the occurrence of engagement of the wheel dressing tool with the area of greatest wear. Although this could be done in many different ways, detecting the occurrence of engagement of the wheel dressing tool with the area of greatest wear is advantageously be done by detecting when a probe member initially engages the area greatest wheel wear.

In accordance with another aspect of the invention, the rotational speed of the grinding wheel is increased as the diameter of the wheel is decreased due to the combined effect of grinding and wheel dressing operations. The rotational speed of the grinding wheel is increased by an amount which is sufficient to maintain a desired wheel surface speed as the diameter of the grinding wheel decreases. Therefore, the wheel surface speed is substantially the same before and after a series of wheel grinding and dressing operations.

Accordingly, it is an object of this invention to provide a new and improved apparatus for dressing a grinding wheel by removing material from the grinding wheel to an extent which is a function of the extent of actual wear at a location where grinding wheel wear is the greatest.

Another object of this invention is to provide a new and improved apparatus in which a member is moved toward the circular side surface of a grinding wheel from a retracted position and includes a detector which detects when the member initially engages the circular side surface of the grinding wheel.

Another object of this invention is to provide a new and improved apparatus as set forth in the preceding object and wherein the detector includes a mass and means for providing an output signal upon relative acceleration between the mass and the member under the influence of forces applied against the member by the grinding wheel upon initial engagement of the member with the grinding wheel.

Another object of this invention is to provide a new and improved apparatus for detecting when a grinding wheel has been fully dressed by detecting when an area on the side surface of the grinding wheel where wear is the greatest is in a predetermined spatial relationship with a wheel dressing tool.

Another object of this invention is to provide a new and improved apparatus which increases the speed at which a grinding wheel is rotated in response to detection of a decrease in grinding wheel diameter.

BRIEF DESCRIPTION OF THE DRAWINGS

The foregoing and other objects and features of the present invention will become more apparent upon a consideration of the following description taken in connection with the accompanying drawings wherein.

DESCRIPTION OF SPECIFIC PREFERRED EMBODIMENTS OF THE INVENTION

Figure 1:
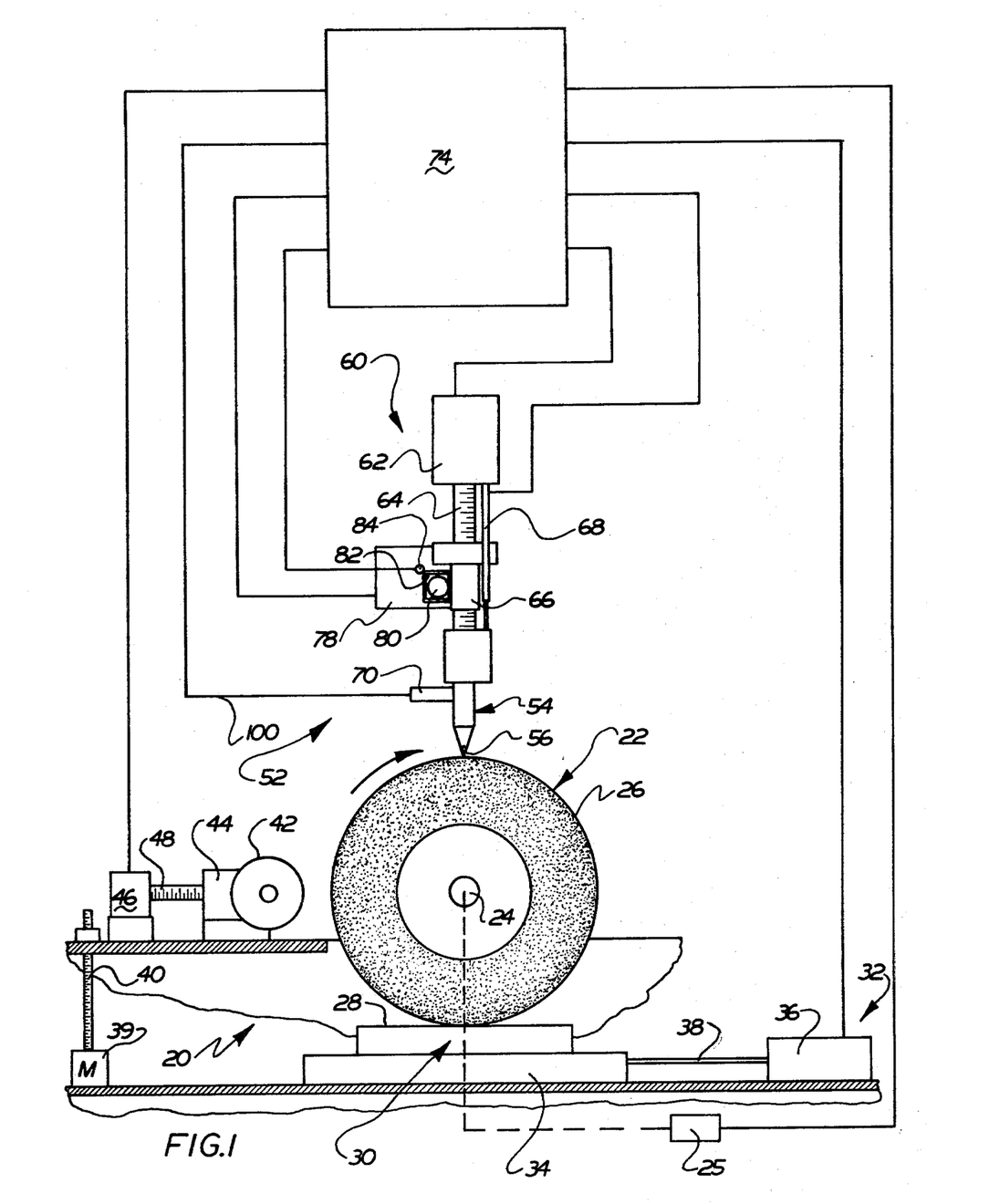
FIG. 1 is a schematic illustration of a grinding apparatus which is constructed and operated in accordance with the present invention.
Figure 2:
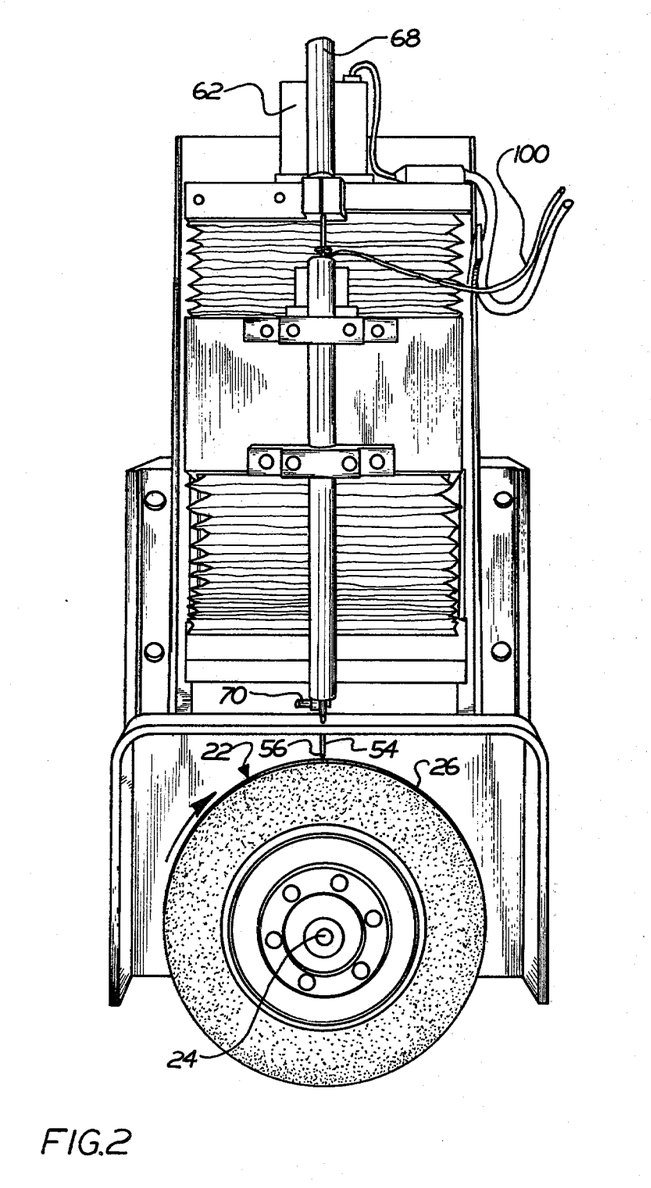
FIG. 2 is a pictorial illustration depicting the relationship between a grinding wheel and a probe member upon initial engagement of the probe member with a circular side surface of the grinding wheel.

A grinding machine 20 which is constructed and operated in accordance with the present invention is illustrated schematically in FIG. 1. The grinding machine 20 includes a circular grinding wheel 22 (FIGS. 1 and 2) which is rotatably supported on a central axle 24 about which it is rotated by a variable speed electric motor 25 (FIG. 1). During operation of the grinding machine 20, a circular outer side surface 26 of the grinding wheel engages a side surface 28 of a workpiece 30. The workpiece 30 is reciprocated along a horizontal path relative to the rotating grinding wheel by a drive assembly 32. The drive assembly 32 includes a slide or carriage 34 upon which the workpiece 30 is disposed and a reversible motor 36 which reciprocates a rod 38 to move the slide 34 toward and away from the grinding wheel 22 in a known manner. The grinding wheel 22 can be moved vertically toward and away from the workpiece 30 by a reversible motor 39 and drive screw 40.

During operation of the grinding machine 20, the circular side surface 26 of the grinding wheel 22 will become worn. Although the grinding wheel 22 could be dressed with any known wheel dressing tool, such as a crush, single point or diamond roll dressing tool, in the illustrated embodiment of the invention a diamond roll wheel dressing tool 42 (FIG. 1) is utilized to dress the grinding wheel 22. The diamond roll dressing wheel 42 is disposed on a slide 44. During wheel dressing operations, the dressing wheel 42 is moved into engagement with the outer side surface 26 of the grinding wheel 22 by operation of a reversible motor 46 to rotate a drive screw 48. The dressing tool 42 removes material from the worn side surface 26 of the grinding wheel to provide the side surface with a desired configuration or contour.

In accordance with a feature of the present invention, an assembly 52 is provided to sense the extent of actual wear of the grinding wheel 22. The assembly 52 includes a probe member or stylus 54 having a wear resistant tip or point 56. A drive assembly 60 (FIG. 1) is operable to move the probe member 54 from a retracted position in which the probe member is spaced a substantial distance from the surface 26 of the grinding wheel 22 to a position (shown in FIGS. 1 and 2) in which the tip 56 of the probe member just barely engages or grazes the outer side surface of the rotating grinding wheel 26.

The drive assembly 60 includes a reversible motor 62 (FIG. 1) which is operable to rotate a drive screw 64. The drive screw 64 cooperates with a nut 66 to effect axially downward movement of the probe member 54 upon rotation of the motor 62 and drive screw 64 in one direction and to effect axially upward movement of the probe member 54 upon rotation of the motor and drive screw in the opposite direction. A transducer 68 provides an output signal indicative of the position of the probe member.

A detector assembly 70 (FIGS. 1 and 2) is provided to detect when the tip 56 initially engages the rotating surface 26 of the grinding wheel as the probe member 54 is moved from the retracted position toward the grinding wheel. Thus, as the motor 62 (FIG. 1) is operated to move the probe member 54 downwardly along a path which extends radially of the grinding wheel 22, the leading end of the tip 56 will initially be engaged by a slightly protruding point on the surface 26 of the grinding wheel. The grinding wheel is rotating at a constant speed in a clockwise direction as viewed in FIGS. 1 and 2. This results in the probe 54 being deflected toward the right (as viewed in FIG. 1) upon initial engagement of the probe member with the rotating grinding wheel 22. The rightward deflection of the probe 54 actuates the detector assembly 70 to provide an output signal to a microprocessor 74 which controls the operation of the probe drive motor 62, the workpiece drive motor 36, the wheel dressing tool drive motor 46, and the grinding wheel drive motor 25. Although a microprocessor 74 is shown in FIG. 1, hard wired circuitry could be utilized if desired.

Upon receipt of a signal indicating that the tip 56 of the probe 54 has initially engaged the peripheral surface of the grinding wheel 22, operation of the motor 60 is immediately interrupted by the microprocessor 74. The position of the probe 54 relative to the central axis of the grinding wheel is transmitted to the microprocessor 74 by the transducer 68. This information is stored in the microprocessor 74. The probe member 54 is then moved away from the grinding wheel 22 to its retracted position by reversing the direction of operation of the motor 62.

The data stored in the microprocessor 74 indicates the position of the probe member 54 when it initially engages the grinding wheel and is indicative of the actual position of the surface 26 of the grinding wheel. The outer surface 26 of a new grinding wheel 22 is initially located before it is utilized to grind the workpiece 30. After the grinding wheel 22 has been used to grind the workpiece 30, the tip of the probe 54 is moved into initial engagement with the grinding wheel in the manner previously explained. The extent of actual wear of the grinding wheel 22 can then be determined by the change in the position of the probe member 54 between the time of engagement with the surface of the new wheel and the time of engagement with the surface of the worn wheel. In one specific preferred embodiment of the invention, the position of the surface 26 of the grinding wheel could be determined to within less than 0.0001 inches by the probe member 54 and detector assembly 70.

During a grinding operation, certain areas on a grinding wheel 22 will wear at a greater rate than other areas of the grinding wheel. The area of greatest wear can be located from prior experience and/or can be predicted using parametric data relating wear to form geometry, wheel speed and rate of feed of the workpiece to the grinding wheel. During a wheel dressing operation, it is necessary to dress the grinding wheel to such an extent that the area of greatest wear is reshaped to the desired configuration. Since the portions of the grinding wheel surface 26 adjacent to the area of greatest wear will have been worn away to a lesser extent, material will be removed from these portions in order to enable the entire working surface 26 of the grinding wheel to be dressed to the desired configuration.

Since the extent to which it is necessary to dress a grinding wheel is determined by the extent of wear at the area where the greatest wear occurs during a grinding operation, the probe 54 is moved into alignment with the area on the grinding wheel 22 which will have the greatest wear. This is accomplished by operating a reversible motor 78 (FIG. 1) to rotate a threaded shaft 80 which is connected with a nut 82. Rotation of the shaft 80 by the motor 78 effects movement of the probe member 54 along a path which extends parallel to the axis of rotation of the grinding wheel 22. This moves the probe 54 into alignment with the circular area which will experience the greatest wear during a grinding operation. A transducer 84 provides the microprocessor 74 with an output signal which is indicative of the position of the probe member 54 along the grinding wheel axis.

Figure 3:
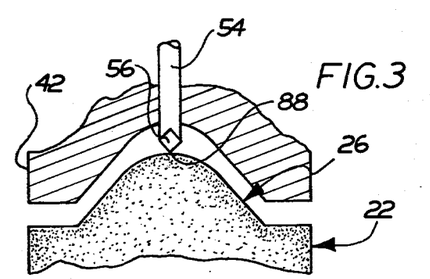
FIG. 3 is a schematic illustration depicting initial engagement of a probe member with an area on the circular side surface of the grinding wheel where the greatest amount of wear will occur during a grinding operation.

The manner in which the probe member 54 engages the area of greatest wear on the circular side surface 26 of a grinding wheel 22 is illustrated schematically in FIG. 3. The area of greatest wear of the particular grinding wheel side surface configuration illustrated in FIG. 3 occurs along a circular band at the crest 88 on the side surface of the grinding wheel. Therefore, when the motor 62 (FIG. 1) is operated to move the probe member 54 into initial engagement with the grinding wheel 22 to detect the extent of wear of the grinding wheel, the wear resistant tip 56 of the probe member is moved into engagement with the crest 88 (FIG. 3) on the grinding wheel surface 26.

When the tip 56 of the probe member 54 initially engages the crest 88 of the grinding wheel surface 26, one or more grains of abrasive material on the grinding wheel 22 impact against the tip of the probe member. The resulting deflection of the probe member 54 is sensed by the detector assembly 70 which signals the microprocessor that initial contact has been made. The output from the transducer 68 (FIG. 1) indicates the position of the probe member relative to the central axis of the grinding wheel at the time of initial engagement. The position of the probe member is stored in the microprocessor 74 which also determines the extent of actual wheel wear.

The probe member 54 is then retracted and a wheel dressing tool 42 is moved toward the grinding wheel by the drive motor 46 through a distance which is a function of the extent of actual wear of the grinding wheel 22. The wheel dressing tool 42 is of the diamond roll type and has a periphery with a configuration which corresponds to the desired configuration of the grinding wheel 22 (see FIG. 3). When the extremely hard peripheral surface of the diamond roll dressing tool 42 is pressed against the grinding wheel 22, the tool removes material from the areas on opposite sides of the crest 88 in the manner illustrated schematically in FIG. 4. It should be noted that the dressing tool 42 does not initially engage the crest 88 of the surface 26 and is initially effective to only remove material from portions of the grinding wheel adjacent to the crest.

Figure 5:
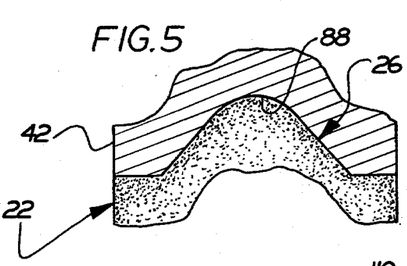
FIG. 5 is a schematic sectional view, generally similar to FIGS. 3 and 4, illustrating the relationship between the grinding wheel and the dressing tool when the grinding wheel has been fully dressed.

As the dressing roll 42 continues to be pressed toward the center of the grinding wheel 22 by operation of the motor 46, the dressing tool 42 moves into engagement with the crest 88 of the grinding wheel 22 in the manner shown in FIG. 5. This shapes the crest 88 to the desired configuration. When the crest 88 of the grinding wheel 22 has been shaped to the desired configuration, the grinding wheel has been fully dressed. Therefore, when the crest 88 has been shaped to the desired configuration, the microprocessor 74 reverses the direction of operation of the motor 46. The wheel dressing tool 42 is then moved to the retracted position shown in FIG. 1.

In this embodiment of the invention, the microprocessor 74 cooperates with the detector assembly 70 to determine the actual location of the most worn area on the grinding wheel 22 relative to the central axis of the grinding wheel. The microprocessor 74 then effects forward operation of the motor 46 to move the wheel dressing tool 42 through a distance which is a function of the actual grinding wheel wear. Thus, the microprocessor 74 interrupts forward operation of the motor 46 when the dressing tool 42 reaches the fully dressed position shown in FIG. 5. This occurs when the most worn area of the grinding wheel, that is the crest 88, has been shaped to the desired configuration. This prevents the removal of an excessive amount of material from the grinding wheel during a wheel dressing operation.

It should be noted that although dressing of the grinding wheel 22 could be interrupted as soon as the crest 88 is shaped to the desired configuration, in actual practice the wheel dressing tool will be moved slightly further toward the center of rotation of the grinding wheel. This removes a small increment of material from the grinding wheel as the safety factor to be sure that the entire surface 26 of the grinding wheel is shaped to the desired configuration.

By utilizing the probe member 54 to detect the extent of wear at the location where the greatest or maximum wear of the grinding wheel 22 will occur, the microprocessor 74 can determine the extent to which the dressing tool 42 must be moved toward the central axis of the grinding wheel 22 in order to properly dress the grinding wheel. If the probe member 54 is aligned with an area of the grinding wheel where less than the maximum amount of wear occurs, the microprocessor 74 multiplies the sensed wear by a factor having a value which is determined by the ratio of the extent of greatest wear to the extent of wear in the area being sensed. However, the necessity of determining this ratio is eliminated by positioning the probe member 54 along the surface of the grinding wheel 22 at a location where radially inward movement of the probe member toward the center of the grinding wheel will result in the probe member moving into initial engagement with the area of the grinding wheel where the greatest amount of wear occurs.

When the grinding wheel 22 is used to grind the workpiece 30, the diameter of the grinding wheel is reduced as material is worn away from the grinding wheel. In addition, the diameter of the grinding wheel 22 is reduced during wheel dressing operations. If the motor 25 continues to rotate the grinding wheel at a constant rotational speed after the diameter of the grinding wheel has been reduced due to grinding and/or wheel dressing operations, the surface speed of the grinding wheel will be reduced by an amount which is a function of the extent of the reduction in grinding wheel diameter.

During grinding operations, the surface speed of the grinding wheel 22 is advantageously maintained substantially constant. Therefore after microprocessor 74 detects the extent of wheel wear prior to the performance of a wheel dressing operation, the microprocessor increases the speed at which the motor 24 rotates the grinding wheel 22 about is central axis to maintain the surface speed of the grinding wheel 22 constant.

The amount by which the rotational speed of the grinding wheel 22 is increased to compensate for a reduction in grinding wheel diameter is a function of the extent to which the diameter of the grinding wheel is reduced. Thus, the motor 25 is operated to drive a new grinding wheel 22 at a predetermined rotational speed so that the grinding wheel has a desired surface speed. After the grinding wheel has been worn away by the workpiece 30, a wheel dressing operation is performed.

Immediately prior to performance of the wheel dressing operation, the probe member 54 is utilized to detect the extent of actual wear of the grinding wheel 22 in the manner previously explained. This enables the microprocessor 24 to determine the extent to which the diameter of the grinding wheel has been reduced by the grinding operation. The diameter of the grinding wheel is reduced in the area of greatest wheel wear by a predetermined minimum amount during wheel dressing operation. Therefore, the microprocessor 74 adds a small factor to the amount of wear which is actually sensed by the probe member 54 to determine the diameter of the grinding wheel after a wheel dressing operation. After the wheel dressing operation, the microprocessor 74 increases the speed at which the motor 25 drives the grinding wheel 22 by an amount which is proportional to the extent to which the diameter was reduced. This results in the surface speed of the grinding wheel being the same after grinding and wheel dressing operations as before the grinding and wheel dressing operations. Of course, the probe member 54 could be used to detect changes in grinding wheel diameter between wheel dressing operations to enable the microprocessor 74 to incrementally increase the speed at which the motor 25 drives the grinding wheel 22 as wheel wear occurs.

In one specific embodiment of the invention, the assembly 70 which detects initial engagement of the probe member 54 with the side surface 26 of the grinding wheel 22 is of the accelerometer type. In this embodiment of the invention, the detector assembly 70 includes a mass 92 (see FIG. 6) which is disposed adjacent to a piezoelectric material, such as a quartz crystal 94. The mass 92 is pressed against the crystal 94 by a suitable spring 95. However, if desired, the mass could be pressed against the crystal 94 by the casing 97.

Figures 4, 6, 7:
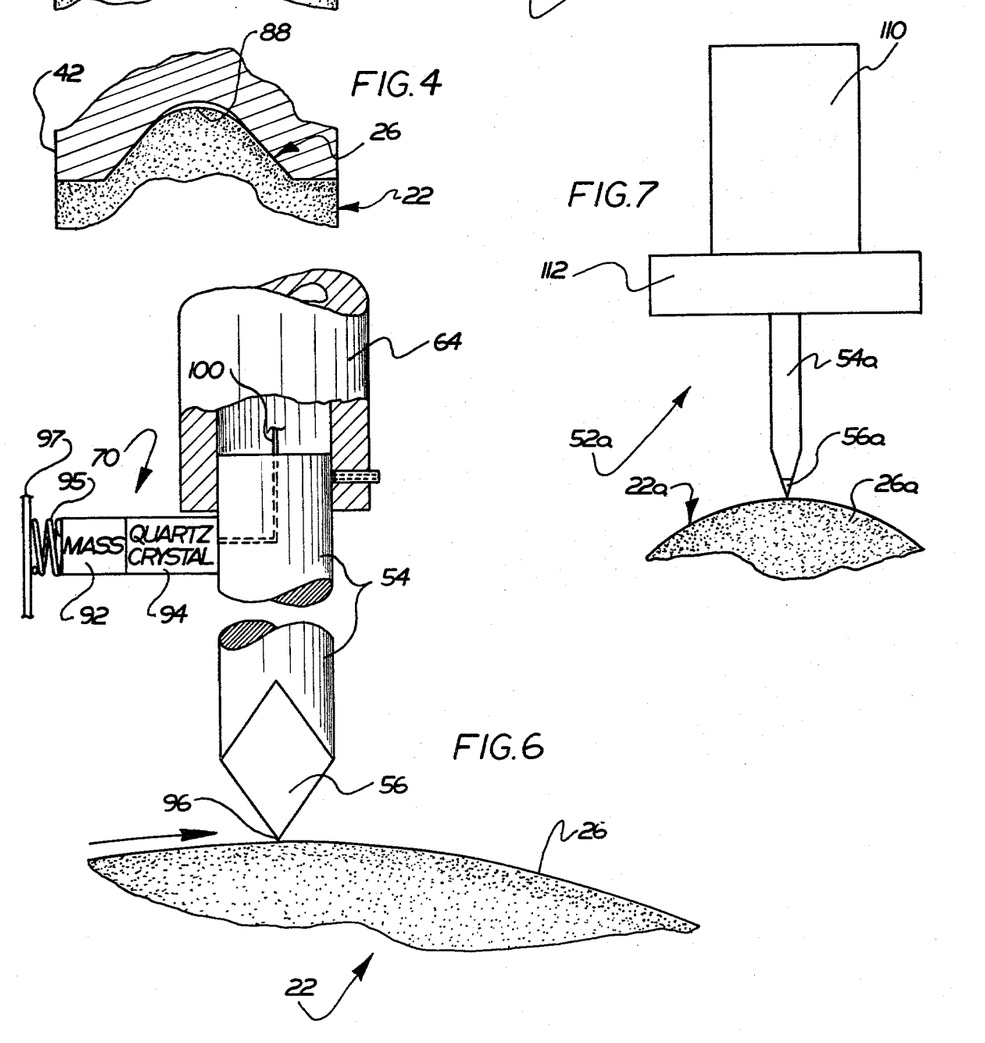
FIG. 4 is a schematic illustration, generally similar to FIG. 3, illustrating the relationship between the grinding wheel and a dressing tool, the grinding wheel being shown in a partially dressed condition.
FIG. 6 is an enlarged fragmentary schematic view illustrating initial engagement of a probe member with the side surface of a grinding wheel and an accelerometer which is activated by forces applied against the probe member upon initial engagement of the probe member with the grinding wheel.
FIG. 7 is a schematic illustration depicting another embodiment of the invention and illustrating initial engagement of a probe member with the side surface of a grinding wheel and a load cell which senses deflection of the probe member.

When the leading end 96 of the tip 56 of the probe 54 initially engages the circular outer side surface 26 of the grinding wheel 22, the probe member 54 is slightly deflected toward the right (as viewed in FIG. 6). This deflection causes relative acceleration between the mass 92 and the probe member 54 to reduce the force applied against the crystal 94. This changes a signal conducted over a lead 100 to the microprocessor 74. Although there are many known types of accelerometers which could be utilized, in one specific instance, the detector assembly 70 was a general purpose accelerometer model No. 508-B sold by BBN Instruments Company of 50 Moulton Street, Cambridge, Mass., 02138 USA. The probe member 54 is moved away from the mass 92 in the illustrated embodiment of the invention. However, the detector assembly 70 could be mounted on the opposite side of the probe member 54 and the probe member moved toward the mass 92 to increase the force applied against the piezoelectric crystal 94 upon engagement of the probe member with the grinding wheel.

The probe drive motor 62 (see FIG. 1) is operated by the microprocessor 74 to quickly move the probe 54 to a position closely adjacent to the grinding wheel 22. The drive motor 62 then continues movement of the probe member 54 toward the grinding wheel 22 through a series of relatively small incremental steps. Each time the probe member is moved through a step by operation of the motor 62, the movement of the prove member is interrupted until the grinding wheel 22 has been rotated through slightly more than a complete revolution by operation of the motor 25.

Sufficient time is allowed between each incremental step of the probe member 54 to enable the grinding wheel 22 to rotate through slightly more than one complete revolution. Therefore, the probe member 54 effectively scans the circumference of the grinding wheel 22 at the area where maximum wear occurs between each incremental step. This results in initial engagement of the leading end 56 of the probe member 54 being a relatively light grazing action which minimizes wear on both the tip of the probe member and the grinding wheel 22.

In order to further minimize wear of the tip 56, a relatively hard diamond tip is advantageously utilized. In fact, in one specific embodiment of the invention, the probe member 54 was actually a diamond tipped wheel dressing tool of the single point type.

In the previously described embodiment of the invention using the model 508-b model accelerometer from BBN Instruments Company, the drive motor 62 was operated to move the probe member 54 through incremental steps of 0.00005 inches. This resulted in the detector assembly 70 being effective to detect the location of the outer side surface 26 of the grinding wheel 22 with an accuracy of 0.0001 inches. In this specific instance, the stepping motor 62 was an eight-phase model HMD 175-2000-8 motor sold by USM Corporation of 51 Armory Street, Wakefield, Mass., 01880, USA. Of course, other known stepping motors could be utilized to effect incremental movement of the probe member through incremental steps of a different size if desired. It should be understood that the specific commercially available models of the stepping motor 62 and the accelerometer type detector assembly 70 have been set forth herein only for purposes of clarity of description and that the invention is not to be limited to any specific model of these devices.

In the embodiment of the invention illustrated in FIG. 6, the accelerometer type detector assembly 70 is utilized to detect when the probe member 54 initially engages the grinding wheel 22. In the embodiment of the invention shown in FIG. 7, a load cell is utilized to detect when the probe member 54 initially engages the grinding wheel by detecting deflection of the probe member under the influence of forces applied against the probe member by the grinding wheel. Since the embodiment of the invention shown in FIG. 7 has many components which are the same as components of the embodiment of the invention shown in FIG. 6, similar numerals will be utilized to designate similar components, the suffix letter "a" being associated with the numerals of FIG. 7 in order to avoid confusion.

The grinding wheel wear detector assembly 52a includes a probe 54a which is moved radially inwardly toward a grinding wheel 22a and axially relative to an outer surface 26a by a drive assembly illustrated schematically at 110. The drive assembly 110 includes a pair of reversible motors corresponding to the motors 62 and 78 in the embodiment of the invention shown in FIG. 1. One of the motors is operable to move the probe member 54a radially relative to the grinding wheel between a retracted position and a position in which a tip 56a of the probe initially engages circular outer surface 26a of the grinding wheel 22a. The other motor is effective to move the probe member 54a along the axis of rotation of the grinding wheel 22a to a position where the probe member is in radial alignment with an area where wear of the grinding wheel will be the greatest during a grinding operation.

In accordance with a feature of this embodiment of the invention, a load cell 112 is connected with the probe member 54a to detect a slight deflection of the probe member which occurs when the tip 56a initially engages the peripheral surface 26a of the grinding wheel 22a. It should be noted that the probe member 54a, like the probe member 54 of FIG. 1, is quickly moved to a position adjacent to the outer surface of the grinding wheel 26a and is then moved through relatively small incremental steps toward the outer surface 26a of the grinding wheel until initial engagement is made with the outer surface 26a of the grinding wheel. Between each of these incremental steps, the grinding wheel 22a rotates through slightly more than one revolution in order to enable the probe member 56a to effectively scan the circumferential area of greatest wear on the surface 26a of the grinding wheel 22a.

Although the load cell 112 has been shown schematically in FIG. 7, it should be understood that the load cell includes a plurality of strain gauges which are interconnected to provide an output to a microprocessor, similar to the microprocessor 74 of FIG. 1. In addition, a dressing tool, similar to the dressing tool 42 of FIG. 1, is provided to dress the grinding wheel 22a to an extent which is determined by the amount of wear at the area of greatest wear on the circular side surface of the grinding wheel. Although the load cell 12 uses strain gauges to detect deflection of probe member 54a, other deflection detector devices such as piezoelectric crystals could be utilized if desired.

Figure 8:
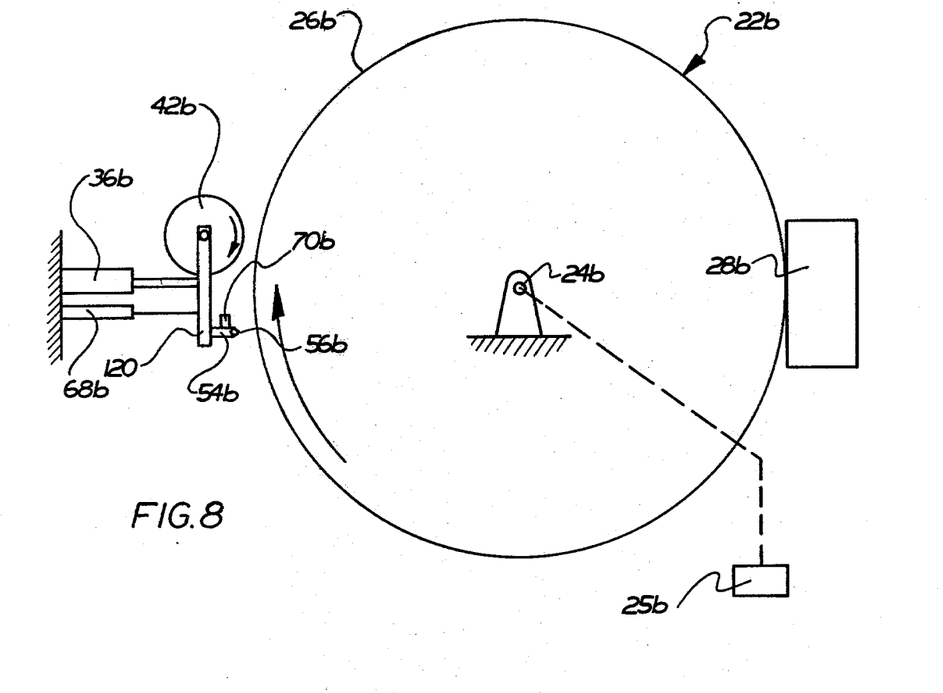
FIG. 8 is a schematic illustration of an embodiment of the invention in which a probe member and wheel dressing tool are moved together toward a circular side surface of a grinding wheel during a wheel dressing operation.
Figure 9:
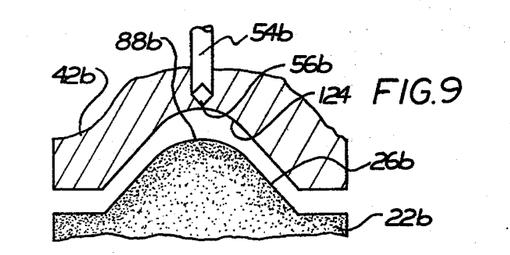
FIG. 9 is a fragmentary schematic illustration, generally similar to FIG. 3, illustrating the relationship between the probe member and wheel dressing tool of the embodiment of the invention shown in FIG. 8, the probe member and wheel dressing tool being shown in their retracted positions.
Figure 10:
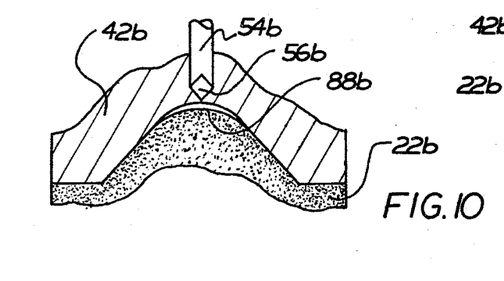
FIG. 10 is a schematic illustration, generally similar to FIG. 9, depicting the relationship between the dressing tool, probe member and grinding wheel when the grinding wheel has been partially dressed.

In the embodiments of the invention shown in FIGS. 1–7, the probe member 54 or 54a is moved into engagement with a grinding wheel to determine the extent of actual wear of the grinding wheel. The grinding wheel is then dressed by an amount which is determined by the extent of actual wear of the grinding wheel. In the embodiment of the invention shown in FIG. 8, the probe member is utilized to detect when the grinding wheel has been fully dressed during a grinding operation. Since the embodiment of the invention shown in FIGS. 8–10 is generally similar to the embodiments of the invention shown in FIGS. 1–7, similar numerals will be utilized to designate similar components, the suffix letter "b" being associated with FIG. 8 to avoid confusioin.

A grinding wheel 22b is rotated at a constant speed about a support 24b by a drive motor 25b. A circular outer side surface 26b of the grinding wheel is effective to grind a workpiece 28b. When the grinding wheel 22b becomes worn, a motor 36b is operated to move a wheel dressing tool 42b into engagement with the circular outer side surface 26b of the grinding wheel to dress the grinding wheel.

In accordance with a feature of this embodiment of the invention, a probe member 54b is moved with the wheel dressing tool by a support 120 which is connected with the motor 36b. The probe member 54b is radially aligned with the area of greatest wear on the outer side surface 26b of the grinding wheel 22b. In addition the probe member is aligned with the wheel dressing tool 42b so that upon initial engagement of a tip 56b of the probe 54b with the area of greatest wear, the grinding wheel 22b will have been fully dressed. As this occurs, an accelerometer type detector 70b mounted on the probe member 54b provides a signal to a microprocessor, similar to the microprocessor 74 of FIG. 1, to indicate that the wheel dressing operation has been completed.

Although the probe member 54b and dressing tool 42b have been shown as being mounted on a common support 120 and as being moved by a single motor 36b, they could be mounted separately and moved in synchronism by a pair of motors. Thus, the probe member 54 of FIG. 1 could be moved by the motor 62 in synchronism with movement of the dressing tool 42 by the motor 46. This would maintain the spatial relationship shown in FIGS. 9-11 between the probe member 54 and dressing tool 42 during dressing of the wheel 22.

Figure 11:
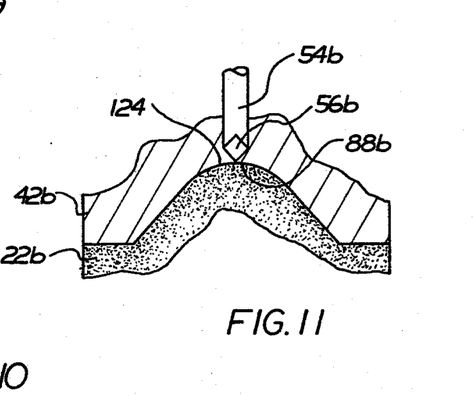
FIG. 11 is a schematic illustration, generally similar to FIG. 10, depicting the relationship between the dressing tool, probe member and grinding wheel when the grinding wheel has been fully dressed.

The manner in which the probe member 54b is moved with the diamond roll wheel dressing tool 42b is indicated schematically in FIGS. 9-11. Before the grinding wheel is to be dressed, the wheel dressing tool 42b and probe member 54b are in a retracted position shown in FIG. 9. It should be noted that the tip 56b of the probe member 54b is aligned with the crest 88b on the grinding wheel surface 26b where the wear will be the greatest during grinding of the workpiece 28b. It should also be noted that the outer end of the tip 56b is aligned with the surface 124 of the wheel dressing tool which will dress the crest 88b. Thus, complete dressing of the crest 88b by the tool 42b will occur simultaneously with initial engagement of the tip 56b with the crest 88b.

When a wheel dressing operation is to be undertaken, the wheel dressing tool 42b and probe 54b are moved together toward the grinding wheel 22b by operation of the motor 36b (see FIG. 8). As the wheel dressing tool 42b is pressed against the outer side surface 26b of the grinding wheel 22b by operation of the motor 36b, the wheel dressing tool 42b will remove material from the circular side surface of the grinding wheel adjacent to the crest 88b where the grinding wheel has been worn down to the greatest extent. During this portion of the wheel dressing operation, the tip 56b of the probe member 54b is spaced from the crest 88b of the grinding wheel.

When the grinding wheel has been fully dressed (see FIG. 11), the crest 88b of the grinding wheel 22b will be disposed in engagement with the surface area 124 of the wheel dressing tool 42b to shape the crest 88b to a desired configuration. In addition, the tip 56b of the probe member 54b will be in initial engagement with the crest 88b of the grinding wheel. When the grinding wheel 22b is fully dressed, as shown in FIG. 11, the tip 56b of the probe member 54b will engage the crest 88b and will be deflected to a relatively small distance. This deflection is sensed by the detector assembly 70b to provide an output signal to an associated microprocessor. A transducer 68b provides an output signal indicative of the position of the probe member 54b and wheel dressing tool 42b.

In the embodiment of the invention illustrated in FIG. 8, the probe member 54b and wheel dressing tool 42b are mounted on a common base 110. It is believed that this mounting arrangement could result in difficulty as the diameter of the grinding wheel is reduced. This is because the geometric relationship between the grinding wheel axis and the central axes of the probe member 54b and the dressing tool 42b change as the diameter of the grinding wheel 22b changes. Therefore, it may be preferred to move the probe member 54b separately from the dressing tool 42b while maintaining the same effective spatial relationship between the probe member 54b and dressing tool 42b shown in FIGS. 9-11. It is contemplated that this could be done by synchronizing separate drive motors for the probe member 54b and wheel dressing tool 42b to maintain the desired spatial relationship between the probe member and dressing tool as they move together along separate paths which extend radially of the grinding wheel.

In view of the foregoing, it is apparent that the present invention provides a new and improved method and apparatus which enables a grinding wheel 22, 22a or 22b to be accurately dressed without excessive removal of material from the grinding wheel. By accurately dressing the grinding wheel without overcompensating for wear, the volume of abrasive material removed from a grinding wheel during each dressing operation is reduced. By reducing the amount of material which is removed from the grinding wheel during each dressing operation, the rate at which the diameter of the grinding wheel is reduced is decreased with the result that the grinding wheel has a relatively high surface speed for a longer period of time which in turn tends to increase wheel life. Thus, wheel life is increased both by reducing the amount of material which is removed during each wheel dressing operation and due to the fact that the wheel surface speed after each dressing operation is faster than with prior art dressing devices and methods. This enhances the operating life of the grinding wheel and reduces the number of times which a grinding machine must be shut down to change a grinding wheel.

In accordance with a feature of the present invention, the extent of actual wear of a grinding wheel surface 22, 22a, or 22b in an area where wear is the greatest is sensed. The grinding wheel 22, 22a or 22b is dressed by removing material from the grinding wheel to an extent which is a function of the extent of the sensed wear at the location where the wear is the greatest. In order to sense the extent of actual wear of the grinding wheel, a probe member 54, 54a or 54b is moved toward the grinding wheel. A detector 70, 112 or 70b is provided to detect when the probe member initially engages the circular side surface of the grinding wheel.

In an embodiment of the invention, the detector which detects the initial engagement of the probe member with a grinding wheel is an accelerometer 70 or 70b. The accelerometer 70 or 70b includes an inertial mass which tends to remain stationary during deflection of the probe member 54 or 54b when it initially engages the grinding wheel 22 or 22b. The acceleration of the mass 92 results in an output signal from a piezoelectric material 94 to indicate the occurrence of deflection of the probe member by the grinding wheel upon initial engagement of the grinding wheel with the probe member. In another embodiment of the invention, deflection of the probe member 54a due to initial engagement with the grinding wheel is detected by a load cell 112.

During the use of a grinding wheel, certain areas, such as the crest 88, will wear at a greater rate than others. It is possible by experimentation and/or calculation to determine the areas of a grinding wheel which wear at the greatest rate. In order to fully dress a grinding wheel, the grinding wheel must be dressed to an extent such that the area of greatest wear is dressed to the desired configuration. In an embodiment of the invention (FIGS. 8–11), completion of a wheel dressing operation is detected by detecting when the area of greatest wear, that is the crest 88b, is in a predeterined spatial relationship with a wheel dressing tool 42b. This is accomplished by detecting the occurrence of engagement of the wheel dressing tool 42b with the area of greatest wear, that is the crest 88b (see FIG. 11). Although this could be done in many different ways, detecting the occurrence of engagement of the wheel dressing tool 42b with the area of greatest wear is advantageously be done by detecting when a probe member 54b initially engages the area of greatest wheel wear.

In accordance with another aspect of the invention, the rotational speed of the grinding wheel 22, 22a or 22b is increased as the diameter of the grinding wheel is decreased due to the combined effect of grinding and wheel dressing operations. The rotational speed of the grinding wheel 22, 22a or 22b is increased by an amount which is sufficient to maintain a desired wheel surface speed as the diameter of the grinding wheel decreases. Therefore, the speed of movement of a point on the side surface 26, 26a or 26b of a grinding wheel is substantially the same before and after a series of wheel grinding and dressing operations.

Having described specific preferred embodiments of the invention, the following is claimed:

1. An apparatus comprising a grinding wheel having a circular side surface for use in grinding a workpiece, a member, motor means for moving said member toward the circular side surface of said grinding wheel from a retracted position in which said member is spaced from the circular side surface of said grinding wheel, drive means for rotating said grinding wheel as said member moves toward the circular side surface of said grinding wheel, detector means for detecting when said member initially engages the circular side surface of said grinding wheel, and control means for effecting operation of said motor means to move said member toward the side surface of said grinding wheel in incremental steps and for interrupting movement of said member between steps for a time period sufficient to enable said drive means to rotate said grinding wheel through at least one complete revolution.

2. An apparatus as set forth in claim 1 wherein said detector means includes a mass, connector means for connecting said mass with said member to enable relative acceleration to occur between said mass and said member under the influence of forces applied against said member upon initial engagement of said member with the circular side surface of said grinding wheel, and means for providing an output signal upon relative acceleration between said mass and said member under the influence of forces applied against said member by said grinding wheel upon initial engagement of said member with the circular side surface of said grinding wheel.

3. An apparatus as set forth in claim 1 wherein said member is resiliently deflectable under the influence of forces applied against said member by said grinding wheel, said detector means including means for detecting deflection of said member.

4. An apparatus as set forth in claim 1 wherein said apparatus further includes wheel dressing means for dressing said grinding wheel by removing material from said grinding wheel.

5. An apparatus comprising a grinding wheel having a circular side surface for use in grinding a workpiece, a member, motor means for effecting relative movement between said member and the circular side surface of said grinding wheel from a first condition in which said member is spaced from the circular side surface of said grinding wheel and a second condition in which said member engages the circular side surface fo said grinding wheel, drive means for rotating said grinding wheel, detector means for detecting when said member and the circular side surface of said grinding wheel move into initial engagement, control means connected with said detector means and said motor means for initiating operation of said motor means to effect relative movement between said member and said grinding wheel from the second condition to the first condition in response to detection by said detector means of initial engagement of said member with the circular side surface of said grinding wheel, and wheel dressing means for dressing said grinding wheel by removing material from said grinding wheel while said member is in the first condition.

6. An apparatus as set forth in claim 5 further including means for connecting said wheel dressing means with said member, said motor means being operable to effect simultaneous movement of said wheel dressing means and said member relative to said grinding wheel.

7. An apparatus as set forth in claim 5 wherein said control means includes means for controlling operation of said motor means to move said member and said grinding wheel relative to each other in incremental steps and for interrupting relative movement between steps for a time period sufficient to enable said drive means to rotate said grinding wheel through at least one complete revolution.

8. An apparatus comprising a rotatable grinding wheel having a circular aide surface for grinding a workpiece, said circular side surface having a first circular area which wears at a first rate during grinding of a workpiece and a second circular area which wears at a second rate which is greater than said first rate during grinding of a workpiece, drive means for rotating said grinding wheel, wheel dressing means for dressing said grinding wheel to a desired configuration after wear of said grinding wheel, said wheel dressing means including a first wheel dressing surface area having a configuration corresponding to the configuration of the first surface area of said grinding wheel and a second wheel dressing area having a configuration corresponding to the configuration of the second surface area of the grinding wheel, motor means for effecting relative movement between said wheel dressing means and said grinding wheel to engage said first circular surface area of said grinding wheel with said first wheel dressing surface area, for continuing relative movement between said wheel dressing means and said grinding wheel to remove material from said grinding wheel with said first wheel dressing area and for moving said second wheel dressing area and said second circular surface area of said grinding wheel into engagement, detector means for detecting when said grinding wheel has been fully dressed to the desired configuration by said wheel dressing means, said detector means including probe means for initially engaging said second circular surface area of said grinding wheel simultaneously with initial engagement of said second wheel dressing area with said second circular surface area of said grinding wheel, and control means for effecting operation of said motor means to move said wheel dressing means and said circular side surface of said grinding wheel out of engagement in response to initial egagement of said second circular area of said grinding wheel with said probe means.

* * * * *

UNITED STATES PATENT AND TRADEMARK OFFICE
CERTIFICATE OF CORRECTION

PATENT NO. : 4,295,301

DATED : October 20, 1981

INVENTOR(S) : Barth et al.

It is certified that error appears in the above-identified patent and that said Letters Patent are hereby corrected as shown below:

Column 14, line 10, change "fo" to --of--.

Column 14, line 39, change "aide" to --side--.

Column 16, line 1, change "egagement" to --engagement--.

Signed and Sealed this

Twenty-sixth Day of February 1985

[SEAL]

Attest:

DONALD J. QUIGG

Attesting Officer     Acting Commissioner of Patents and Trademarks